United States Patent [19]

Gram

[11] Patent Number: 4,809,556

[45] Date of Patent: Mar. 7, 1989

[54] PRELOADING CLAMP

[75] Inventor: Martin M. Gram, St. Louis Park, Minn.

[73] Assignee: MTS Systems Corporation, Eden Prairie, Minn.

[21] Appl. No.: 99,483

[22] Filed: Sep. 22, 1987

[51] Int. Cl.$^4$ .............................................. G01N 3/02
[52] U.S. Cl. ........................................ 73/856; 403/43; 411/263
[58] Field of Search .................... 403/43, 46, 47, 44, 403/45, 48, 344, 110, DIG. 7; 411/263, 307, 998, 433, 511, 259; 73/856

[56] References Cited

U.S. PATENT DOCUMENTS

| | | | |
|---|---|---|---|
| 1,167,758 | 1/1916 | Hess | 403/344 X |
| 2,783,809 | 3/1957 | Haines | 403/47 X |
| 3,320,798 | 5/1967 | Gram | 73/103 |
| 3,335,603 | 8/1967 | Gram | 73/103 |
| 4,326,406 | 4/1982 | Smith | 73/49.1 |

FOREIGN PATENT DOCUMENTS 500078 2/1954 Canada .................................. 403/43

OTHER PUBLICATIONS

Brochure: "V-Band Couplings," Voss Industries, Inc.
"Fatigue Testing of Medical Sutures," *Closed Loop*, MTS Systems, Inc., Fall 1986, pp. 12–17.
Catalog: "Grips and Fixtures Catalog," MTS Systems, Inc. 1986.

*Primary Examiner*—Jerry W. Myracle
*Attorney, Agent, or Firm*—Kinney & Lange

[57] ABSTRACT

A clamp for use in testing machines to prestress a joint between a driving shaft and a driven shaft, both of which are externally threaded with each having a flat surface abutting the other in a plane substantially perpendicular to the driving axis. The clamp is internally threaded to cooperate with the external threads and has bolts which, when tightened, produce a force on the abutting surfaces to compressively preload the joint from forces on the flanks of the external threads.

13 Claims, 1 Drawing Sheet

PRELOADING CLAMP

BACKGROUND OF THE INVENTION

1. Field of the Invention.

This invention relates to a clamp for use in, for example, tension and compression testing machines and more particularly to a clamp useful to prestress the joint between a grip which holds the workpiece being tested and the piston rod connected to the actuator which applies the compression and tension forces.

2. Description of the Prior Art.

Tests involving repeated applications of stress, called fatigue tests, are usually performed by cyclic compression and tension. Examples of machines used in fatigue tests may be seen in the M. M. Gram U.S. Pat. No. 3,320,798 assigned to the assignee of the present invention. As can be seen in this patent, a reciprocating actuator operates to cyclically move an actuator rod or shaft back and forth. The actuator rod is connected to a grip device which is operable to hold the specimen being tested. The grip device is connected to the actuator rod or shaft by means of a threaded connection between the grip and the actuator rod to hold the two together.

Other methods of joining the grip to the actuator rod are also usable. For example, a V-band coupling manufactured by Voss Industries, Inc., of Cleveland, Ohio, could encompass a pair of flanges extending radially out from the joining ends of the grip and actuator rod which would then be tightened to secure the two members together in a rigid manner.

SUMMARY OF THE INVENTION

The present invention differs from the prior art by using the split clamp to prestress the joint between two rods or shafts, one of which is on a grip for a tensile test machine and the other of which may be an actuator rod or a shaft from a load cell. A pilot member may be provided in, for example, the actuator rod or shaft to fit within an aperture in the grip shaft so as to assure lateral alignment. More particularly, the ends of the actuator rod and of the grip shaft are machined so as to be substantially perpendicular to the axis of the cyclical force application, and the apparatus is assembled by abutting the two perpendicular surfaces together with the pilot member in the aperture and placing the split clamp loosely therearound in such a manner that internal threads on the split clamp cooperate with threaded portions on the actuator rod and the grip shaft. In the preferred embodiment, the threads on the actuator rod are cut with opposite inclination (right hand) to the threads on the grip (left hand) so that when the clamp is fitted onto the external threads and then turned, the abutting surfaces are pushed together to produce a slight compressional force and the flanks or sides of the threads which carry tensile loads are engaged.

The clamp can be built with both the actuator and the grip having right-hand or left-hand threads. The grip then must be rotated relative to the piston rod to tighten the two parts together in order to produce the desired loading on the thread flanks. The clamp bolts on the split clamp are then tightened, which causes a force on only the tensile flank of the threads and causes an increase in compressional force at the joint between the perpendicular ends of the actuator rod and the grip shaft. The clamp bolts are then tightened sufficiently to insure that the compression force at the joint is greater than the tension force which will be encountered during testing and accordingly the joint is preloaded to a value such that the abutting surfaces always are under compressional force during use and the cyclical actuator will not increase the load on the threads. By prestressing in this manner, the fatigue load on the threads is significantly reduced while alignment of the two shafts is accurately achieved through known and simple machining techniques.

DETAILED DESCRIPTION OF THE PREFERRED EMBODIMENTS

Figure 1:
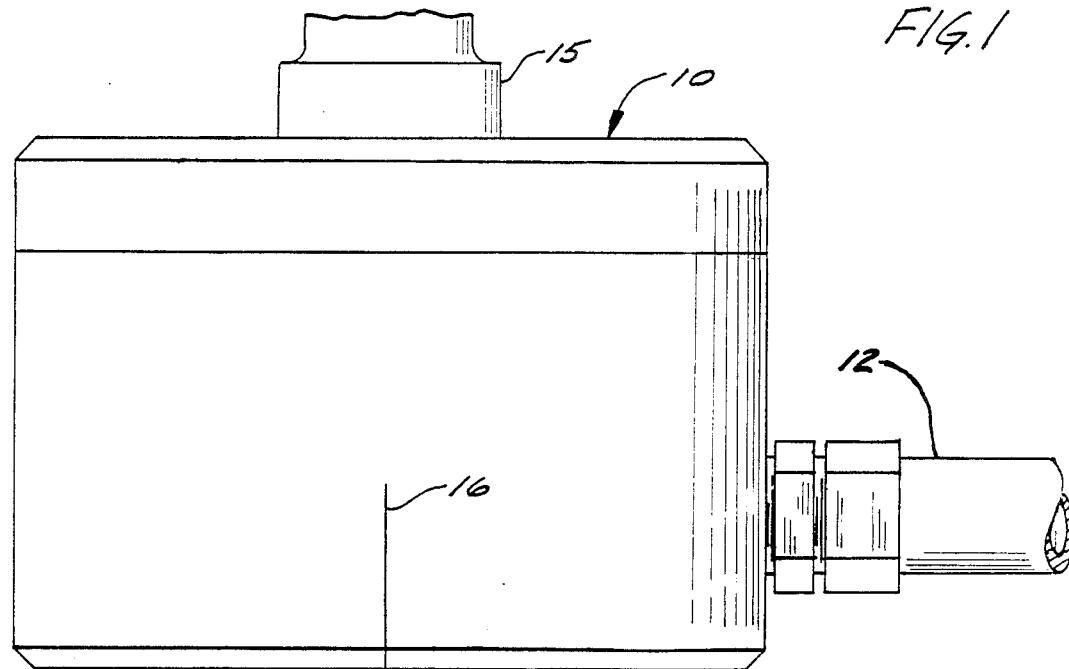
FIG. 1 is a cross-sectional side view of the joint between an actuator shaft and a specimen grip taken along lines 1—1 of FIG. 2.

FIG. 1 shows a specimen grip 10 with hydraulic connections 12 used in actuation thereof to produce a clamping force for holding a specimen 15 on which tension and compression forces will be applied along an axis 16.

A grip shaft 20 is shown having an externally threaded portion 22 which, in the preferred embodiment, may be inclined as a left-handed thread of predetermined pitch.

An actuator rod or shaft 30 connected to a conventional hydraulic actuator 31 is shown having an externally threaded portion 32 which, in the preferred embodiment, is inclined as a right-handed thread having a pitch which may be the same as (or different from) threads 22. The preloading arrangement of the present invention is useful where reciprocating or torsional loads are being applied to a specimen held in the grip. The actuator shaft 30 thus is reciprocated along axis 16 or is rotated on axis 16 (or both) with the hydraulic actuator 31.

A lower end surface 36 of shaft 20 and an upper end surface 38 of shaft 30 are precisely machined to be substantially perpendicular to axis 16. End surface 36 has an aperture 42 therein and end surface 38 has a pilot pin 44 thereon sized to fit within the aperture 42 for alignment purposes when end surfaces 36 and 38 are butted together to form a joint therebetween. Because of the pilot pin 44 and the machined end surfaces 36 and 38, the lateral and axial angular alignment will be substantially exact.

Figure 2:
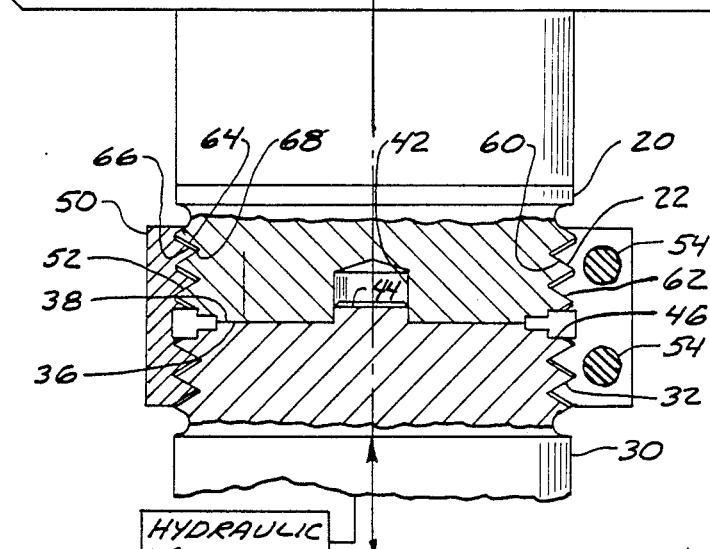
FIG. 2 is a top view of the split clamp shown in position to encompass the shaft and grip.
Figure 2:
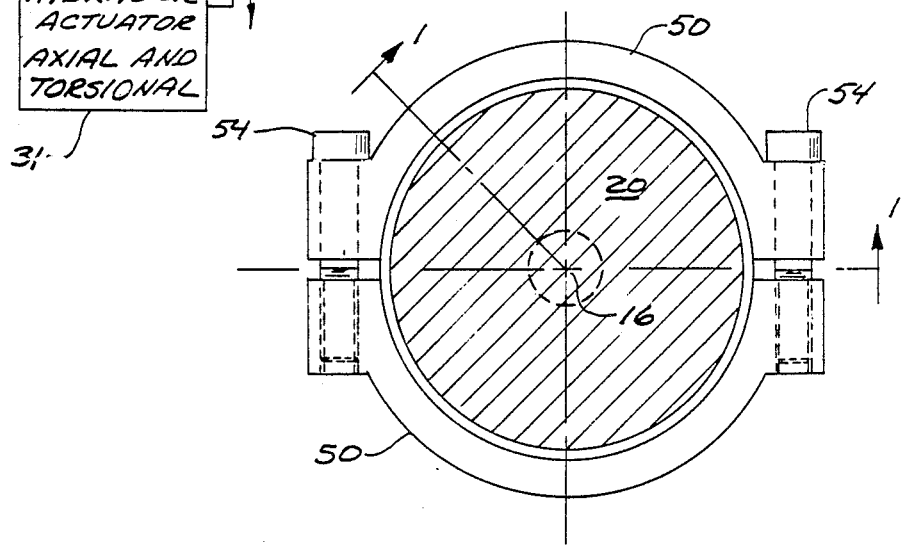

A split clamp 50 is shown having internal threads as at 52 of substantially the same pitch as threads 22 and 32, and having a left-handed section and a right-handed section so as to cooperate with the threads 22 and 32, respectively. Split clamp 50 has a plurality of clamp bolts 54, best seen in FIG. 2, which, when tightened, operate to pull the two halves of split clamp 50 together.

In order to provide a preload condition at the joint between end surfaces 36 and 38, the split clamp 50 is placed loosely around the shafts 20 and 30. The clamp 50 is rotated manually to an orientation with respect to the shafts 20 and 30 until the internal threads 52 of split clamp 50 mesh with both the upper and lower threads 22 and 32 of shafts 20 and 30, respectively. The bolts 54 are placed loosely in the clamp 50. Thereafter, clamp 50 may be lightly rotated so as to produce a small compression force on the abutting surfaces 36 and 38 between shafts 20 and 30. With the shafts 20 and 30 now being laterally well aligned with the axes of the two shafts 20 and 30 coincident, the bolts 54 can be tightened to produce the desired prestressed condition. It will be noted that tightening bolts 54 causes the effective thread pitch diameter of the clamp to be reduced causing additional compressional forces to be exerted at the end surfaces of the shafts 20 and 30 by virtue of the flank angle of the threads which produces a force on only the tensile flank of the threads. The "tensile flank" means the thread flank that produces tensile forces in the clamp 50 and compressive forces on the ends of the shafts 20 and 30. For example, it can be seen in FIG. 1 that a tensile flank 60 of the threads 22 on shaft 20 is being forced toward a tensile flank 62 of the threads 52 on clamp 50. The other flank 64 of the threads 22 on shaft 20 is shown to receive no force from the other flank 66 of the threads on split clamp 50. This is shown in FIG. 1 by the slight space 68 therebetween (shown exaggerated for clarity).

The same situation is true with respect to the tensile flank of the threads 32 on shaft 30 and accordingly it can be seen that a compressional force on the end surfaces 36 and 38 can be applied which is greater than the tensile force applied on the actuator to preload the joint so it will not move or misalign during use. The threads 22 and 32 are of sufficient number so that the stress is low and their fatigue life considerably extended.

In the preferred embodiment, the threads of shaft 20 have been inclined in a left-handed manner while the threads of shaft 30 have been inclined in a right-handed manner which allows the shafts to be oriented and then the clamp 50 rotated to the position where the clamp fits both threads and then the clamp further rotated to load the proper thread flank before torquing the bolts. However, other arrangements are possible. For example, the threads of both the upper and lower shafts 20 and 30 could have the same direction of lead of the threads, which would allow the clamp to be oriented in any direction, but in this event the joint parts must then be rotated relative to each other to tighten the joint in preparation for torquing the clamp bolts for preloading. Also, the threads on the shafts do not have to have the same pitch nor do they have to have the same diameter as long as the internal threads of the clamp match them.

The end surfaces at the joint are preloaded to a level proportional to the torque on the bolts 54 and, by making the stiffness of the joint much greater through the end surfaces of the shafts than the axial stiffness of the clamp, then the fatigue component of the load is primarily transmitted in compression through the shaft end surfaces and the fatigue rated design is much smaller than the previous design with the same fatigue rating which had not been axially preloaded. The stiffness of the joint can be made greater than the axial stiffness of the clamp by making the clamp relatively thin and highly stressed, which has an additional cost advantage.

Torsional movements can also be transmitted with this device, either separately or in combination with axial loads. The torque applied (torsional loading) is transmitted by a combination of friction on the ends of the piston rod and grip and by friction on the clamp threads. The walls of clamp 50 must be made thick enough to carry the shear forces generated by the torque loading in addition to the tensile forces caused by the axial preload.

The reciprocating and torsional loading of a specimen can be accomplished using an axial-torsional load frame, for example, the 309 Series load frame made by MTS Systems Corporation of Eden Prairie, Minn.

It should also be noted that two sets of bolts are not necessary in that the clamp can have a hinge or a pivot hook on one side and the bolts on the opposite side. The feature of being able to tighten the clamp to compress the end of the shafts 20 and 30 together can be accomplished with adjustable fasteners on only one side of the clamp.

Although the present invention has been described with reference to preferred embodiments, workers skilled in the art will recognize that changes may be made in form and detail without departing from the spirit and scope of the invention. For example, the pilot 44 may be on shaft 20 and aperture 42 on shaft 30 instead of the reverse, as shown. Likewise, other types of actutors may be utilized instead of a hydraulic actuator.

What is claimed is:

1. A loaded joint comprising:
    a first member having a threaded portion and an end with a surface substantially perpendicular to an axis;
    a second member having a threaded portion and an end with a surface substantially perpendicular to an axis, the end of the first member abutting the end of the second member with the axes substantially colinear to form a joint; and
    split clamp means including clamp bolt means for tightening the split clamp means, the split clamp means being internally threaded and surrounding the first and second members so that the threaded portions of the first and second members cooperate with the internal threading of the split clamp means and the clamp bolt means being tightened to apply a compression force on the first and second members to cause a compression force on the abutting surfaces of the first and second members.

2. Apparatus according to claim 1 wherein the threaded portion of the first member is a right-hand thread of predetermined pitch and the threaded portion of the second member is a left-hand thread of predetermined pitch.

3. Apparatus according to claim 1 wherein an aperture is formed in the end of the first member and a pilot is formed in the end of the second member sized to fit within the aperture to assure lateral alignment.

4. Apparatus according to claim 3 wherein the threaded portions of the first and second members are of opposite inclination but of the same pitch.

5. Apparatus according to claim 1 wherein the threaded portions are of the same inclination and of the same pitch.

6. Apparatus according to claim 1 wherein the threaded portions are of different pitch.

7. Apparatus according to claim 1 wherein the split clamp means comprises two clamp sections and clamp bolt means on opposite sides of the first and second members tightenable to move the clamp sections together.

8. The method of preloading a joint between a first cylindrical member having a first axis and a first threaded portion, and a second cylindrical member having a second axis and a second threaded portion, comprising the steps of:
    forming a first end surface on said first member substantially perpendicular to the first axis;
    forming a second end surface on said second member substantially perpendicular to the second axis;

placing the first and second members with the first and second end surfaces abutting and the first and second axes substantially colinear to form a joint;

placing a split clamp with an internally threaded portion and clamp bolts around the first and second members with the internally threaded portion engaging the first and second threaded portions;

orienting the clamp to produce engagement on the thread flanks that produce compression forces on the ends of the first and second members and tensile forces in the clamps; and tightening the clamp bolt which will produce a compression force on the first and second end surfaces to preload the joint and to produce a reaction force on the tensile flank of the threads of the first and second threaded portions.

9. The method of claim 8 in which the step of placing the split clamp around the first and second members includes the step of placing the clamp bolts loosely therein.

10. The method of claim 9 further including the step of rotating the first member until the internally threaded portion of the split clamp meshes with both the threaded portions of the first and second members.

11. A compression loaded joint comprising:
a first member having a longitudinal axis;
a second member having a longitudinal axis;
the first and second members each having means thereon forming abutting end surfaces to hold the axes of both members substantially colinear to form a joint;
threadable means connected to each of said first and second member adjacent the joint for coupling the first and second members together;
split clamp means having internal threads with tapered thread flanks, and positioned to the exterior of the first and second members so that the threadable means of the first and second members interfit with the internal threading of the split clamp means before the internal threading on the split clamp means and the threadable means are fully seated in radial direction, when the end surfaces of the first and second members are abutting; and means for tighteing the split clamp means radially inwardly on the threadable means for applying a force between the thread flanks to apply compression force on the abutting end surfaces of the first and second members through the threadable means to seat the members under compression at the joint.

12. The loaded joint of claim 11 and cooperating interfitting means on the first and second members, respectively, to form pilot means for retaining the first and second members co-linear when the abutting surfaces are placed under compression.

13. The method of preloading a joint between a first member having a first axis and a second member having a second axis, comprising the steps of:

forming a first end surface on said first member substantially perpendicular to the first axis;

forming a second end surface on said second member substantially perpendicular to the second axis;

placing the first and second members with the first and second end surfaces abutting and the first and second axes substantially colinear to form a joint;

providing first and second sets of external threads having thread flanks that taper outwardly and which are operable for applying compressive loads to end surfaces of the first and second members, respectively;

placing a split clamp with an internally threaded portion and clamp bolts around the first and second members with the internally threaded portion engaging the first and second sets of external threads;

orienting the clamp to produce engagement of the internal threads on the thread flanks of the first and second sets of external threads; and tightening at least one clamp bolt to reduce the effective diameter of the internal threaded portion and produce a compression force on the first and second end surfaces through the thread flanks and to produce a reaction force on the thread flanks of the sets of external threads.

* * * * *